(12) United States Patent
Hillman

(10) Patent No.: US 8,814,992 B2
(45) Date of Patent: Aug. 26, 2014

(54) GAS EXPANSION COOLING METHOD

(75) Inventor: Brandon Paul Hillman, Lafayette, LA (US)

(73) Assignee: Greene's Energy Group, LLC, Houston, TX (US)

( * ) Notice: Subject to any disclaimer, the term of this patent is extended or adjusted under 35 U.S.C. 154(b) by 273 days.

(21) Appl. No.: 13/485,467

(22) Filed: May 31, 2012
(Under 37 CFR 1.47)

(65) Prior Publication Data

US 2013/0072740 A1    Mar. 21, 2013

Related U.S. Application Data

(60) Provisional application No. 61/492,190, filed on Jun. 1, 2011.

(51) Int. Cl.
| | | |
|---|---|---|
| *B01D 53/00* | (2006.01) | |
| *F25J 1/00* | (2006.01) | |
| *C07C 7/04* | (2006.01) | |

(52) U.S. Cl.
CPC ............. *F25J 1/0022* (2013.01); *B01D 53/002* (2013.01); *B01D 2257/702* (2013.01); *C07C 7/04* (2013.01)
USPC .............................................. 95/288; 62/611

(58) Field of Classification Search
USPC .............................................. 95/288; 62/611
See application file for complete search history.

(56) References Cited

U.S. PATENT DOCUMENTS

| | | |
|---|---|---|
| 2,004,074 A | 6/1935 | Kiley |
| 3,464,230 A | 9/1969 | Rietdijk et al. |
| 4,077,789 A | 3/1978 | Edwards |
| 4,727,723 A | 3/1988 | Durr |
| 5,038,583 A | 8/1991 | Gali |
| 5,234,552 A | 8/1993 | McGrew et al. |
| 5,850,857 A | 12/1998 | Simpson |
| 5,857,338 A | 1/1999 | Rigal |
| 5,860,294 A | 1/1999 | Brendeng |
| 5,897,690 A | 4/1999 | McGrew |
| 2002/0170312 A1 | 11/2002 | Reijnen et al. |

FOREIGN PATENT DOCUMENTS

JP         02268808 A    *   11/1990   ................... 422/177

OTHER PUBLICATIONS

PCT International Searching Authority/US, International Search Report and Written Opinion of the International Searching Authority, mailed Aug. 22, 2012, for PCT/US2012/40353, "Gas Expansion Cooling Method."

* cited by examiner

*Primary Examiner* — Robert A Hopkins
(74) *Attorney, Agent, or Firm* — Jones Walker LLP

(57) ABSTRACT

A gas expansion cooling method for reducing hydrocarbon emissions includes feeding a high pressure cooling gas through a valve, decreasing a temperature of the cooling gas by decreasing its pressure; feeding the cooling gas into a heat exchanger; and diverting a hydrocarbon gas into the heat exchanger such that the cooling gas decreases a temperature of the hydrocarbon gas. The cooling gas may be drawn from a preexisting high pressure gas system that serves a purpose other than supplying a coolant for the gas expansion cooling system. A portion of the hydrocarbon gas may be condensed in the heat exchanger to form a hydrocarbon liquid, which may be separated from the hydrocarbon gas in a separation vessel. The hydrocarbon liquid may be recovered, while the hydrocarbon gas may be fed to a ventilation system.

23 Claims, 2 Drawing Sheets

GAS EXPANSION COOLING METHOD

CROSS REFERENCE TO RELATED PATENT APPLICATIONS

This application claims priority to U.S. Provisional Application No. 61/492,190, filed on Jun. 1, 2011, which is incorporated herein by reference.

DETAILED DESCRIPTION OF THE PREFERRED EMBODIMENTS

The United States Environmental Protection Agency (EPA) regulates the emission of harmful vapors into the air. For example, the EPA regulates the release of volatile organic compounds (VOCs) and mono-nitrogen oxides (NOx). VOCs are organic chemicals that have high vapor pressures at ambient conditions due to low boiling points. Many VOCs are dangerous to human health or harmful to the environment. It has been established that many petroleum products are not only toxic, but are also carcinogens. This is especially true of many of the lighter fractions of petroleum products, formed of relatively light weight molecules and having relatively high vapor pressures. In the past, these products were routinely vented to the atmosphere. The EPA now regulates the release of hydrocarbon vapors and VOCs into the atmosphere. The Clean Air Act requires that Maximum Achievable Control Technology (MACT) removes VOCs with at least 95% efficiency.

A method for cooling a fluid using a gas cooled by a decrease in pressure (i.e., an expansion of the gas). The cooling gas may be supplied by a preexisting gas line on a job location having a high pressure. The preexisting gas line may be present on the job location for a purpose other than for use of the gas as a coolant. For example, gas recovered from an oil and gas well may be compressed before being transported by pipeline. A portion of the high pressure gas exiting the compressor may be diverted for use as a cooling gas in a heat exchanger for cooling another fluid. The high pressure gas may be cooled by flowing through a pressure reduction valve, such as a Joule-Thomson valve (JT valve), which causes the gas to expand thereby decreasing the temperature of the gas. This cooling gas may be fed into the shell portion of a heat exchanger, while a fluid is fed through an inner portion of the heat exchanger. The fluid flowing through the inner portion of the heat exchanger is cooled by the cooling gas flowing through the shell portion. After exiting the heat exchanger, the cooling gas may be returned to the compressor.

The gas expansion cooling method may include cooling a high pressure gas by decreasing the pressure, and causing the cooled gas to flow through a heat exchanger to cool and/or condense another fluid flowing through the heat exchanger.

Figure 1:
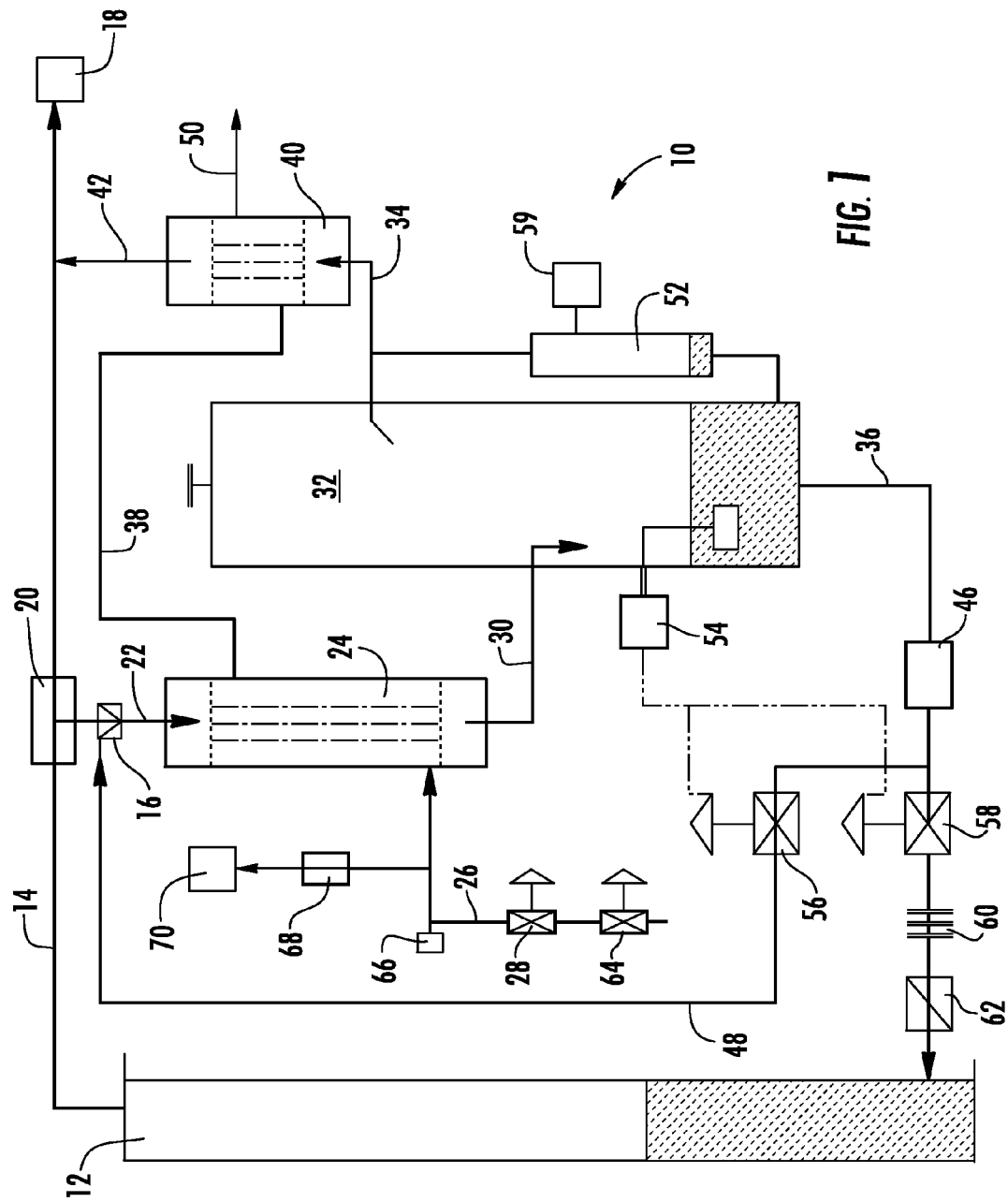
FIG. 1 is a schematic view of the equipment involved in the gas expansion cooling method used to cool hydrocarbon vapors from a hydrocarbon storage tank.

One application for the gas expansion cooling method is in the control of emissions from hydrocarbon storage tanks, such as the method disclosed in U.S. Pat. No. 5,897,690, issued to Robert L. McGrew on Apr. 27, 1999, which is incorporated herein by reference. Gas expansion cooling system 10 for cooling hydrocarbon vapors from source 12 is illustrated in FIG. 1. In one embodiment, source 12 may be a hydrocarbon storage tank. Certain types of hydrocarbons held in storage tanks vaporize within the tanks. These hydrocarbon vapors may flow into vapor line 14. Atomizer 16 may assist in the flow of the hydrocarbon vapors into vapor line 14 through the creation of a slight vacuum. Vapor line 14 may ultimately lead to ventilation system 18, but three way valve 20 positioned on vapor line 14 may divert the hydrocarbon vapors into hydrocarbon input line 22. The hydrocarbon vapors may flow through hydrocarbon input line 22. In some embodiments, the hydrocarbon vapors may contain small amounts of impurities, such as water vapor. Atomizer 16 may be a nozzle or other spraying device, and it may be positioned on hydrocarbon input line 22. Alternatively, atomizer 16 may be positioned within an inner portion of heat exchanger 24. Atomizer 16 may create a slight vacuum in hydrocarbon input line 22 as described in more detail below. The hydrocarbon vapors may flow into an inner portion of heat exchanger 24. In one embodiment, the hydrocarbon vapors may flow into a tube portion of heat exchanger 24.

A cooling gas may enter gas cooling system 10 through cooling gas input line 26. In one embodiment, the cooling gas may be supplied by a preexisting gas line on a job location having a high pressure. For example, the cooling gas may be a portion of the process gas from an oil & gas well. The high pressure cooling gas may be cooled by flowing through valve 28 on cooling gas input line 26. Valve 28 may cause the cooling gas to expand by forcing it through a restriction orifice, thereby decreasing the pressure and temperature of the gas. In this way, the hydrocarbon gas is cooled through expansion. Valve 28 may be any type of pressure reduction valve, such as a JT valve. The cooling gas may be cooled to a predetermined temperature based on the composition of the hydrocarbon gas in hydrocarbon input line 22. In one embodiment, the cooling gas may be cooled to about 40° F. The cooling gas may be fed into a shell portion of heat exchanger 24.

The cooling gas flowing through the shell portion of heat exchanger 24 may cool the hydrocarbon vapor flowing through the inner portion of heat exchanger 24, thereby condensing the heavier and more harmful hydrocarbons in the hydrocarbon vapor in the inner portion. The remaining hydrocarbon vapors and the condensed hydrocarbon fluid may flow from the inner portion of heat exchanger 24, through hydrocarbon fluid output line 30, and into separation vessel 32. The hydrocarbon fluid flowing through hydrocarbon fluid output line 30 may be mostly liquid with only trace amounts of hydrocarbon vapors. The remaining hydrocarbon vapors in separation vessel 32 include only lighter hydrocarbons (e.g., methane, ethane). The remaining hydrocarbon vapors and the condensed hydrocarbon fluid separate in separation vessel 32. The remaining hydrocarbon vapors rise within separation vessel 32 and exit through hydrocarbon gas output line 34. The condensed hydrocarbon fluid settles to the bottom of separation vessel 32, and exits through hydrocarbon liquid output line 36. In some embodiments, additional amounts of the hydrocarbon liquid may vaporize while in separation vessel 32 depending upon ambient temperatures and the length of time the hydrocarbon liquid remains in separation vessel 32 before exiting through hydrocarbon liquid output line 36. These additional vaporized hydrocarbons may also rise within separation vessel 32 and exit through hydrocarbon gas output line 34. The cooling gas may flow from the shell portion of heat exchanger 24 and into cooling gas output line 38.

Cooling gas output line 38 may feed the cooling gas into a shell portion of second heat exchanger 40, while hydrocarbon gas output line 34 may feed the remaining hydrocarbon vapors into an inner portion of second heat exchanger 40. The cooling gas may cool the remaining hydrocarbon vapors in second heat exchanger 40, thereby condensing any residual heavy hydrocarbons in the remaining hydrocarbon vapor. Any condensed hydrocarbons may drain from the inner portion of second heat exchanger 40 back into hydrocarbon gas output line 34 and separation vessel 32. The remaining hydrocarbon vapors may exit second heat exchanger 40 through second hydrocarbon gas output line 42 and into vapor line 14, which may direct the remaining hydrocarbon vapors to ventilation system 18. Ventilation system 18 may include a vapor recovery system or a flare. Alternatively, ventilation system 18 may vent the remaining hydrocarbon vapors to the atmosphere.

The composition of the hydrocarbon vapors in lines 14, 22, 30, 34, and 42 may vary. For example, vapor line 14 and hydrocarbon input line 22 may contain the highest concentration of VOCs or heavier hydrocarbon vapors. Hydrocarbon fluid output line 30 may contain hydrocarbon vapors and hydrocarbon liquids. The hydrocarbon vapors in line 30 may contain a lower concentration of VOCs or heavier hydrocarbon vapors, as these vapors may have condensed in heat exchanger 24. Second hydrocarbon gas output line 42 may contain a lower concentration of VOCs or heavier hydrocarbon vapors than hydrocarbon gas output line 34.

Hydrocarbon liquid output line 36 may feed the condensed hydrocarbon fluid from separation vessel 32 to source 12. Alternatively, hydrocarbon liquid output line 36 may feed the condensed hydrocarbon fluid from separation vessel 32 into a collection vessel separate from source 12. Pump 46 may assist in transporting the condensed hydrocarbon fluid through hydrocarbon liquid output line 36. A portion of the condensed hydrocarbon fluid may be diverted from hydrocarbon liquid output line 36 and into atomizer feed line 48, which may feed the cool condensed hydrocarbon fluid to atomizer 16. Atomizer feed line 48 may be positioned downstream from pump 46 on hydrocarbon liquid output line 36. Atomizer 16 may spray the condensed hydrocarbon fluid into the hydrocarbon vapor in hydrocarbon input line 22. Because the spray of condensed hydrocarbon fluid is cooler than the hydrocarbon vapor, the hydrocarbon vapor is cooled and the pressure of the hydrocarbon vapor is decreased, thus creating a slight vacuum that may help to draw the hydrocarbon vapors from source 12 and into vapor line 14. This pre-cooling step performed with atomizer 16 may increase the condensing efficiency of heat exchanger 24. In an alternative embodiment, gas expansion cooling system 10 may include one or more atomizers positioned within the inner portion of heat exchanger 24. In another alternative embodiment, one or more atomizers may be positioned within hydrocarbon gas output line 34 from separation vessel 32 to improve the efficiency of condensing heavier hydrocarbon vapors. Any condensed hydrocarbon fluid from this secondary cooling step may be drained into separation vessel 32, and returned to source 12. In yet another alternative embodiment, gas expansion cooling system 10 may include no atomizers.

The cooling gas may exit the shell portion of second heat exchanger 40 through second cooling gas output line 50, which may return the cooling gas to its original position at the job location. For example, if the cooling gas was taken from a preexisting high pressure gas system on a job location, second cooling gas output line 50 may return the cooling gas to a low pressure gas system. Alternatively, if a low pressure system is not available, a gas booster may be positioned on second cooling gas output line 50 to compress the cooling gas, which may then be fed into the high pressure gas system.

If the cooling gas is a hydrocarbon gas, second cooling gas output line 50 may feed the cooling gas to a fuel line, and the cooling gas may be used as a fuel on the job location. None of the gas in the high pressure system is lost through its use as a cooling gas. All of the cooling gas is recovered. In a more specific example, if the cooling gas was taken from a high pressure hydrocarbon gas pipeline, second cooling gas output line 50 may return the cooling gas to an inlet (or low pressure side) of a compressor in the pipeline in order to increase the pressure of the cooling gas to the pressure it had when taken into cooling gas input line 26. Alternatively, if the compressor is already functioning at its intended capacity, a gas booster may be positioned on second cooling gas output line 50 to compress the cooling gas, which may then be fed into an outlet line (or high pressure side) of the compressor or into a pipeline directly.

Gas expansion cooling system 10 may further include level indicator 52 designed to indicate the level of the condensed hydrocarbon fluid within separation vessel 32. Level control 54 may be designed to adjust a setting of control valve 56 on atomizer feed line 48 and control valve 58 on hydrocarbon liquid output line 36. In one embodiment, control valve 56 may be a "normal open" valve, which has an open default position and a closed position when activated, while control valve 58 may be a "normal closed" valve, which has a closed default position and an open position when activated. With the default settings in this embodiment, the condensed hydrocarbon fluid may flow through hydrocarbon liquid output line 36 and into atomizer feed line 48. In this embodiment, when level control 54 detects a predetermined liquid level within separation vessel 32, level control 54 may activate control valves 56 and 58 such that control valve 56 closes and control valve 58 opens in order to drain the condensed hydrocarbon fluid from separation vessel 32 into hydrocarbon liquid output line 36 and back into source 12. Level safety high control 59 may detect when a fluid level in level indicator 52 reaches a level safety high.

Meter 60 may be positioned on hydrocarbon liquid output line 36, and may be designed to measure the amount of condensed hydrocarbon fluid returned to source 12. Flow safety valve 62 may be positioned on hydrocarbon liquid output line 36 near source 12 in order to prevent the flow of hydrocarbon liquids from source 12 back into hydrocarbon liquid output line 36. Shutdown valve 64 positioned on cooling gas input line 26 may be designed to stop the flow of the cooling gas through cooling gas input line 26 in the event that the fluid level in separation vessel 32 rises above a predetermined safe limit or in the event that the pressure rises above a predetermined safe limit. Thermostat 66 may be positioned on cooling gas input line 26 in order to indicate the temperature of the cooling gas in the cooling gas input line 26. Pressure safety valve 68 may be positioned on a conduit leading from cooling gas input line 26. Pressure safety valve 68 may be designed to measure the pressure of the cooling gas, and to open if the measured pressure value is above a predetermined pressure limit in order to vent some of cooling gas to ventilation system 70. Ventilation system 70 may be the same system as ventilation system 18. Alternatively, ventilation system 70 may be separate from ventilation system 18.

If level safety high control 59 detects that the level safety high is reached in level indicator 52, it may isolate gas expansion cooling system 10 by closing shutdown valve 64 to stop the flow of the cooling gas into cooling gas input line 26, shutting down pump 46 to stop the flow of the condensed hydrocarbon fluid from separation vessel 32, and adjusting three way valve 20 to prevent the hydrocarbon vapors in vapor line 14 from entering hydrocarbon input line 22. Gas expansion cooling system 10 may include further safety and measuring devices or, alternatively, may not include one or more of devices 52-70.

Figure 2:
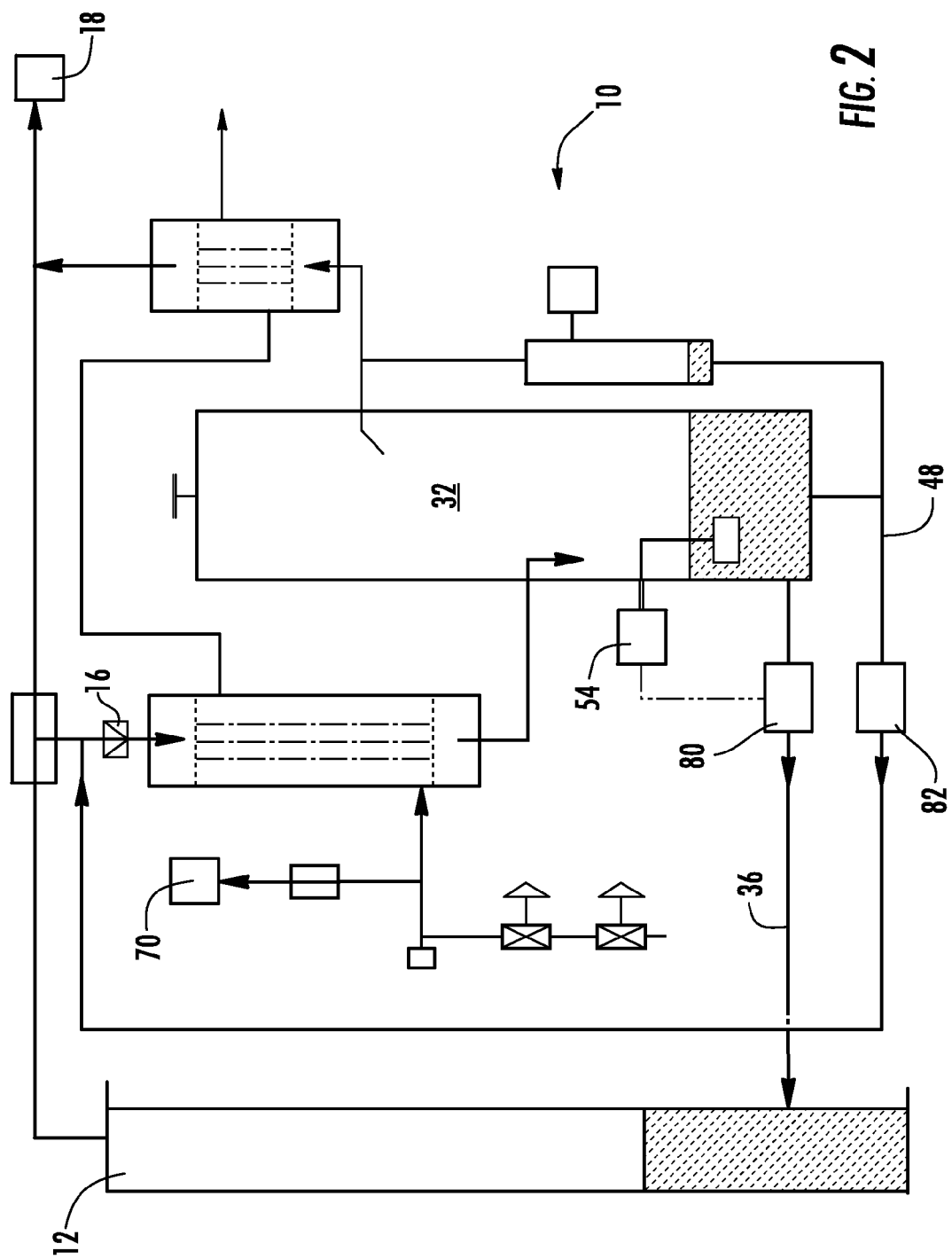
FIG. 2 is a schematic view of an alternate equipment arrangement for the gas expansion cooling method shown in FIG. 1.

FIG. 2 illustrates an alternative embodiment of gas expansion cooling system 10. In this embodiment, hydrocarbon liquid output line 36 may lead the condensed hydrocarbon fluid from separation vessel 32 and into source 12. First pump 80 may be positioned on hydrocarbon liquid output line 36 to assist in returning the condensed hydrocarbon fluid to source 12. In this embodiment, atomizer feed line 48 may lead a portion of the condensed hydrocarbon fluid directly from separation vessel 32 to atomizer 16. Second pump 82 may be positioned on atomizer feed line 48. Level control 54 may be designed to activate first pump 80 on hydrocarbon liquid output line 36 when a predetermined liquid level is reached in separation vessel 32 such that the condensed hydrocarbon fluid is drained from separation vessel 32, thereby lowering the liquid level in separation vessel 32.

Another application for the gas expansion cooling method is in the control of emissions from glycol reboilers, such as the method disclosed in U.S. Pat. No. 5,234,552, issued to Robert McGrew and John P. Broussard on Aug. 10, 1993, which is incorporated herein by reference. The gas expansion cooling method may be used for cooling steam and hydrocarbon vapors from a glycol reboiler. Glycol reboilers are designed to remove water from glycol after its use as a desiccant. Steam and vaporized hydrocarbons exiting the glycol reboiler are fed into an inner portion of a heat exchanger, while an atomizer sprays the steam and vaporized hydrocarbons with a cooling fluid and while a cooling fluid is fed into a shell portion of the heat exchanger. The cooling fluid may be a portion of the hydrocarbon gas line exiting a compressor at a high pressure, which is then cooled through expansion as described above in connection with the hydrocarbon storage tank application. This cooling gas is fed through the shell portion of the heat exchanger and may be returned to any low pressure system or the inlet (or low pressure side) of a compressor. Alternatively, if the compressor is already functioning at its intended capacity, the cooling gas leaving the heat exchanger may be compressed using a gas booster and then fed into the outlet line (or high pressure side) of the compressor or into the pipeline directly. No process gas (or cooling gas) is lost through its use as a cooling gas; all of the process gas is recovered.

The gas expansion cooling method may be used where a coolant is not readily available, but where a high pressure gas system is available. The method may be used in other applications, including, but not limited to, the cooling in rotating equipment lube oil systems, cooling in oil/liquid hydrocarbon cooler systems, or cooling in any hydrocarbon vapor emission systems.

The Clean Air Act requires that Maximum Achievable Controlled Technology (MACT) be at least 95% efficient in removing VOCs from vapor emission streams. Independent tests have shown that a similar method was more than 96% efficient at VOC removal using a cooling fluid having the same temperature as the cooling gas in this method.

The gas expansion cooling method may utilize the energy released by dropping the high pressure gas to a lower pressure gas. In this situation, the method has little to no operating cost. A return on investment may be achieved through the sale of recovered liquid hydrocarbons. The return volume will be determined by the API gravity ("American Petroleum Institute" gravity) of the hydrocarbon along with other factors. In a test model using small storage tanks, returns were between two and three barrels per day. In this situation, the return on investment was approximately $200-300 per day.

While preferred embodiments of the present invention have been described, it is to be understood that the embodiments are illustrative only and that the scope of the invention is to be accorded a full range of equivalents, many variations and modifications naturally occurring to those skilled in the art from a review hereof.

The invention claimed is:

1. A gas expansion cooling method for reducing hydrocarbon emissions, comprising the steps of:
   a) feeding a cooling gas through a valve, wherein the valve decreases a temperature of the cooling gas by decreasing the pressure of the cooling gas;
   b) feeding the cooling gas into a heat exchanger, wherein the cooling gas is drawn from a preexisting high pressure gas system, and wherein the high pressure gas system serves a purpose other than supplying a coolant to the heat exchanger;
   c) diverting a hydrocarbon gas into the heat exchanger such that the cooling gas decreases a temperature of the hydrocarbon gas, wherein a portion of the hydrocarbon gas is condensed by the cooling gas to form a hydrocarbon liquid; and
   d) returning the cooling gas from the heat exchanger into the high pressure gas system.

2. The gas expansion cooling method of claim 1, wherein in step (b), the cooling gas is fed into a shell portion of the heat exchanger; and wherein in step (c), the hydrocarbon gas is diverted into a tube portion of the heat exchanger.

3. The gas expansion cooling method of claim 1, further comprising the steps of:
   e) feeding the hydrocarbon gas and the hydrocarbon liquid from the heat exchanger into a separation vessel; and
   f) allowing the hydrocarbon liquid to separate from the hydrocarbon gas in the separation vessel.

4. The gas expansion cooling method of claim 3, further comprising the steps of:
   g) feeding the hydrocarbon liquid from the separation vessel into a storage vessel; and
   h) feeding the hydrocarbon gas from the separation vessel to a ventilation system;
   wherein the hydrocarbon gas in step (h) contains less VOCs than the hydrocarbon gas fed into the heat exchanger in step (c).

5. The gas expansion cooling method of claim 3, further comprising the steps of:
   g) feeding the cooling gas from the heat exchanger into a second heat exchanger;
   h) feeding the hydrocarbon gas from the separation vessel into the second heat exchanger such that the cooling gas again decreases the temperature of the hydrocarbon gas, wherein a portion of the hydrocarbon gas is condensed by the cooling gas in the second heat exchanger to form a second hydrocarbon liquid.

6. The gas expansion cooling method of claim 5, further comprising the step of:
   i) feeding the second hydrocarbon liquid into the separation vessel.

7. The gas expansion cooling method of claim 6, further comprising the steps of:
   j) feeding the hydrocarbon liquid and the second hydrocarbon liquid from the separation vessel into a storage vessel; and
   k) feeding the hydrocarbon gas from the second heat exchanger to a ventilation system;
   wherein the hydrocarbon gas in step (k) contains less VOCs than the hydrocarbon gas fed into the heat exchanger in step (c).

8. The gas expansion cooling method of claim 3, further comprising the step of:
 g) feeding a cool liquid through an atomizer, the atomizer spraying the cool liquid onto the hydrocarbon gas before it is fed into the heat exchanger such that the cool liquid reduces the temperature of the hydrocarbon gas, thereby creating a vacuum in the hydrocarbon gas.

9. The gas expansion cooling method of claim 8, wherein the cool liquid comprises a portion of the hydrocarbon liquid; and wherein step (g) further comprises: feeding the portion of the hydrocarbon liquid from the separation vessel and through the atomizer, wherein the atomizer sprays the portion of the hydrocarbon liquid onto the hydrocarbon gas before it is fed into the heat exchanger such that the portion of the hydrocarbon liquid reduces the temperature of the hydrocarbon gas, thereby creating a vacuum in the hydrocarbon gas.

10. The gas expansion cooling method of claim 3, further comprising the step of:
 g) feeding a cool liquid through an atomizer, the atomizer spraying the cool liquid onto the hydrocarbon gas as it is fed into the heat exchanger such that the cool liquid reduces the temperature of the hydrocarbon gas, thereby creating a vacuum in the hydrocarbon gas.

11. The gas expansion cooling method of claim 10, wherein the cool liquid comprises a portion of the hydrocarbon liquid; and wherein step (g) further comprises: feeding the portion of the hydrocarbon liquid from the separation vessel and through the atomizer, wherein the atomizer sprays the portion of the hydrocarbon liquid onto the hydrocarbon gas as it is fed into the heat exchanger such that the portion of the hydrocarbon liquid reduces the temperature of the hydrocarbon gas, thereby creating a vacuum in the hydrocarbon gas.

12. A gas expansion cooling method for reducing hydrocarbon emissions, comprising the steps of:
 a) providing a gas expansion cooling system comprising: a cooling gas input line leading to a heat exchanger, a valve disposed on said cooling gas input line, a hydrocarbon input line leading to the heat exchanger;
 b) feeding a cooling gas through the cooling gas input line, the valve, and into the heat exchanger, wherein the cooling gas is drawn from a preexisting high pressure gas system, wherein the high pressure gas system serves a purpose other than supplying a coolant for the gas expansion cooling system, and wherein the valve decreases a temperature of the cooling gas by decreasing the pressure of the cooling gas;
 c) diverting a hydrocarbon gas into the heat exchanger such that the cooling gas decreases a temperature of the hydrocarbon gas, wherein a portion of the hydrocarbon gas is condensed by the cooling gas in the heat exchanger to form a hydrocarbon liquid; and
 d) returning the cooling gas from the heat exchanger into the high pressure gas system.

13. The gas expansion cooling method of claim 12, wherein in step (b), the cooling gas is fed into a shell portion of the heat exchanger; and wherein in step (c), the hydrocarbon gas is diverted into a tube portion of the heat exchanger.

14. The gas expansion cooling method of claim 12, wherein the gas expansion cooling system further comprises a hydrocarbon fluid output line leading from the heat exchanger to a separation vessel, wherein the method further comprises the steps of:
 e) feeding the hydrocarbon gas and the hydrocarbon liquid from the heat exchanger, through the hydrocarbon fluid output line, and into the separation vessel; and
 f) allowing the hydrocarbon liquid to separate from the hydrocarbon gas in the separation vessel.

15. The gas expansion cooling method of claim 14, wherein the gas expansion cooling system further comprises a hydrocarbon liquid output line running from the separation vessel to a storage vessel, and a vent line running from the separation vessel to a ventilation system;
 wherein the method further comprises the steps of:
 g) feeding the hydrocarbon liquid from the separation vessel, through the hydrocarbon liquid output line, and into the storage vessel; and
 h) feeding the hydrocarbon gas from the separation vessel, through the vent line, and to the ventilation system;
 wherein the hydrocarbon gas in step (h) contains less VOCs than the hydrocarbon gas fed into the heat exchanger in step (c).

16. The gas expansion cooling method of claim 14, wherein the gas expansion cooling system further comprises a hydrocarbon gas output line leading from the separation vessel to a second heat exchanger, and a cooling gas output line leading from the heat exchanger to the second heat exchanger, wherein the method further comprises the steps of:
 g) feeding the cooling gas from the heat exchanger, through the cooling gas output line, and into the second heat exchanger;
 h) feeding the hydrocarbon gas from the separation vessel, through the hydrocarbon gas output line, and into the second heat exchanger such that the cooling gas again decreases the temperature of the hydrocarbon gas, wherein a portion of the hydrocarbon gas is condensed by the cooling gas in the second heat exchanger to form a second hydrocarbon liquid.

17. The gas expansion cooling method of claim 16, further comprising the step of:
 i) allowing the second hydrocarbon liquid to drain from the second heat exchanger, through the hydrocarbon gas output line, and into the separation vessel.

18. The gas expansion cooling method of claim 17, wherein the gas expansion cooling system further comprises a hydrocarbon liquid output line running from the separation vessel to a storage vessel, and a vent line running from the second heat exchanger to a ventilation system;
 wherein the method further comprises the steps of:
 j) feeding the hydrocarbon liquid from the separation vessel, through the hydrocarbon liquid output line, and into the storage vessel; and
 k) feeding the hydrocarbon gas from the second heat exchanger, through the vent line, and to the ventilation system;
 wherein the hydrocarbon gas in step (k) contains less VOCs than the hydrocarbon gas fed into the heat exchanger in step (c).

19. The gas expansion cooling method of claim 14, wherein the gas expansion cooling system further comprises an atomizer positioned on the hydrocarbon input line, and wherein the method further comprises the step of:
 g) feeding a cool liquid through the atomizer and into the hydrocarbon input line such that the cool liquid reduces the temperature of the hydrocarbon gas flowing through the hydrocarbon input line, thereby creating a vacuum in the hydrocarbon input line.

20. The gas expansion cooling method of claim 19, wherein the gas expansion cooling system further comprises an atomizer feed line leading from the separation vessel to the atomizer; wherein the cool liquid comprises a portion of the hydrocarbon liquid from the separation vessel; and wherein step (g) further comprises: feeding the portion of the hydrocarbon liquid from the separation vessel, through the atomizer feed line, through the atomizer, and into the hydrocarbon input line such that the portion of the hydrocarbon liquid reduces the temperature of the hydrocarbon gas flowing through the hydrocarbon input line, thereby creating a vacuum in the hydrocarbon input line.

21. The gas expansion cooling method of claim 14, wherein the gas expansion cooling system further comprises an atomizer positioned at an inlet to the tube portion of the heat exchanger, and wherein the method further comprises the step of:
   g) feeding a cool liquid through the atomizer and into the inlet to the tube portion of the heat exchanger such that the cool liquid reduces the temperature of the hydrocarbon gas flowing through the inlet to the tube portion of the heat exchanger, thereby creating a vacuum in the inlet to the tube portion of the heat exchanger.

22. The gas expansion cooling method of claim 21, wherein the gas expansion cooling system further comprises an atomizer feed line leading from the separation vessel to the atomizer; wherein the cool liquid comprises a portion of the hydrocarbon liquid from the separation vessel; and wherein step (g) further comprises: feeding the portion of the hydrocarbon liquid from the separation vessel, through the atomizer feed line, through the atomizer, and into the inlet to the tube portion of the heat exchanger such that the portion of the hydrocarbon liquid reduces the temperature of the hydrocarbon gas flowing through the inlet to the tube portion of the heat exchanger, thereby creating a vacuum in the inlet to the tube portion of the heat exchanger.

23. The gas expansion cooling method of claim 12, wherein step (c) further comprises: diverting a gas mixture into the heat exchanger such that the cooling gas decreases a temperature of the gas mixture, wherein the gas mixture comprises steam and a hydrocarbon gas, and wherein a portion of the gas mixture is condensed by the cooling gas in the heat exchanger to form a liquid mixture comprising water and a liquid hydrocarbon.

* * * * *